US009668719B2

(12) United States Patent
Tegels

(10) Patent No.: US 9,668,719 B2
(45) Date of Patent: Jun. 6, 2017

(54) VASCULAR CLOSURE DEVICES COMPRISING FORCE MANAGEMENT FEATURES AND RELATED METHODS

(71) Applicant: ST. JUDE MEDICAL PUERTO RICO LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 596 days.

(21) Appl. No.: 13/770,832

(22) Filed: Feb. 19, 2013

(65) Prior Publication Data

US 2014/0236222 A1    Aug. 21, 2014

(51) Int. Cl.
*A61B 17/00* (2006.01)
*A61B 34/00* (2016.01)
*A61B 90/00* (2016.01)

(52) U.S. Cl.
CPC .......... *A61B 17/0057* (2013.01); *A61B 34/76* (2016.02); *A61B 2017/00115* (2013.01); *A61B 2017/00402* (2013.01); *A61B 2017/00557* (2013.01); *A61B 2017/00623* (2013.01); *A61B 2017/00659* (2013.01); *A61B 2017/00734* (2013.01); *A61B 2090/064* (2016.02); *A61B 2090/0807* (2016.02)

(58) Field of Classification Search
CPC ...... A61B 17/0057; A61B 2017/00623; A61B 2017/0057; A61B 2017/00115; A61B 2017/00659; A61B 2019/4836; A61B 2019/464; A61M 39/06; A61M 2039/2606
See application file for complete search history.

(56) References Cited

U.S. PATENT DOCUMENTS

| 5,700,277 | A  | * | 12/1997 | Nash et al. ..................... 606/213 |
| 2003/0040737 | A1 | * | 2/2003 | Merril et al. ...................... 606/1 |
| 2009/0248064 | A1 | * | 10/2009 | Preinitz ......................... 606/213 |
| 2009/0254110 | A1 | * | 10/2009 | Bagaoisan et al. ........... 606/185 |
| 2010/0211000 | A1 | * | 8/2010 | Killion et al. .................. 604/57 |
| 2011/0066181 | A1 | * | 3/2011 | Jenson ............... A61B 17/0057 606/213 |

\* cited by examiner

*Primary Examiner* — Anh Dang
(74) *Attorney, Agent, or Firm* — Holland & Hart

(57) ABSTRACT

A vascular closure device may comprise an elongate shaft, a vascular sealing structure, and a carriage. The vascular sealing structure may be located on the elongate shaft and configured to apply a pressure to an interior wall of a lumen. The carriage may be slidably coupled to the elongate shaft, and at least one elastically deformable structure may be configured to transfer at least a portion of a force applied to the carriage to the elongate shaft. A method of vascular closure may comprise positioning a vascular sealing structure located on the elongate shaft within a lumen, transferring at least a portion of a force applied to a carriage to the elongate shaft via at least one elastically deformable structure, and applying a pressure to an interior wall of the lumen with the vascular sealing structure to close a vascular opening.

17 Claims, 7 Drawing Sheets

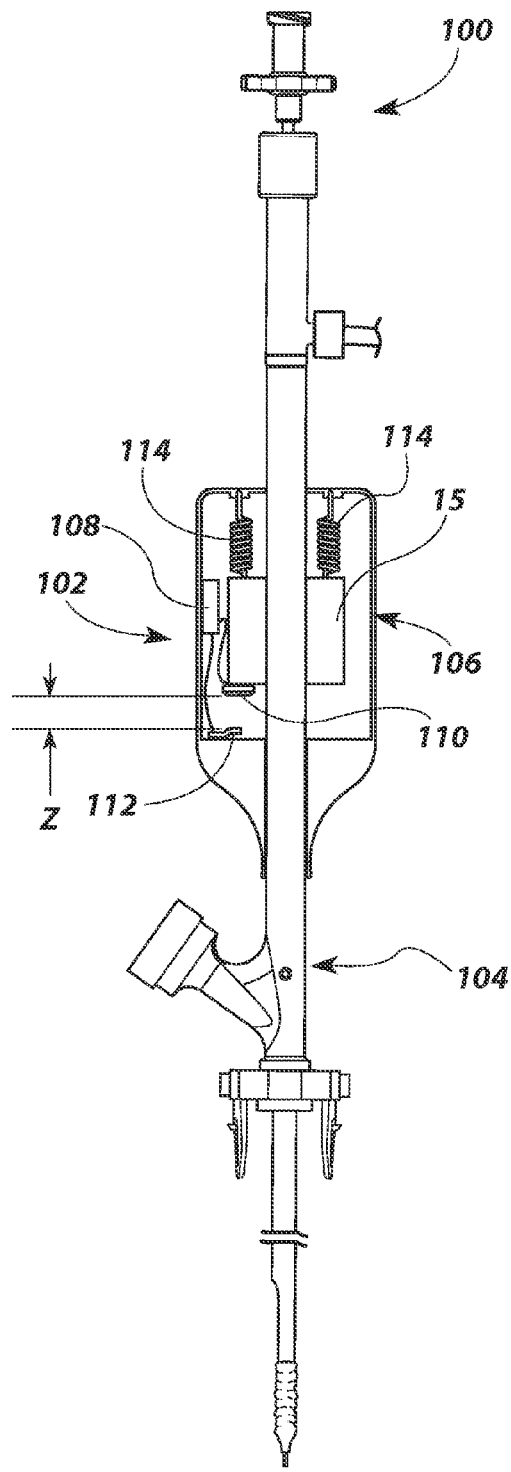 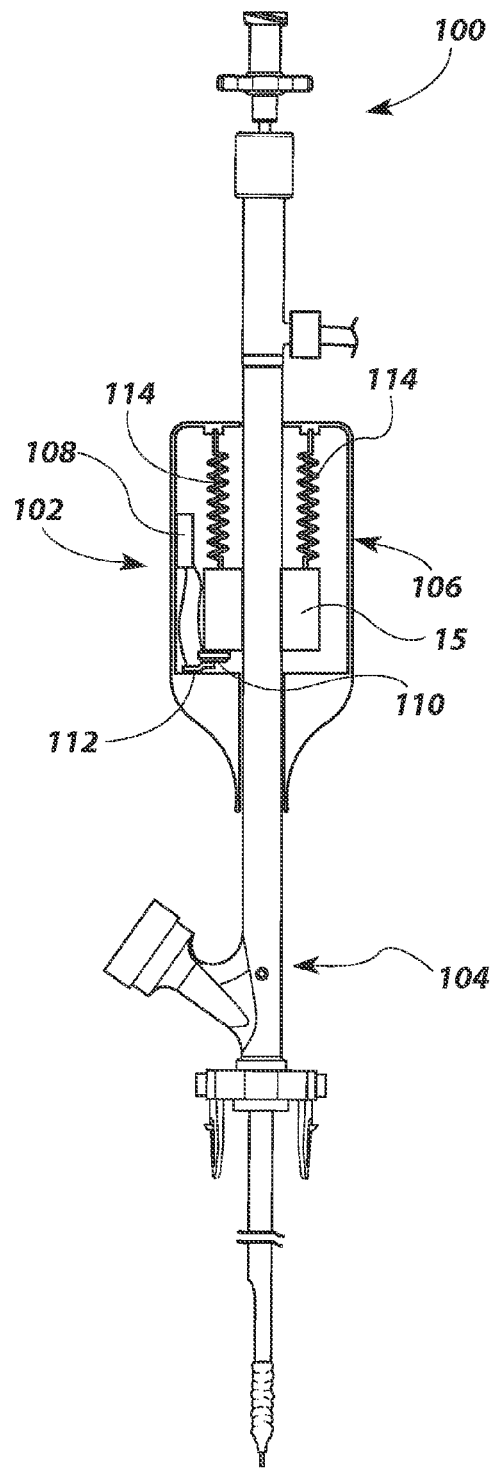
*FIG. 9*  *FIG. 10*

VASCULAR CLOSURE DEVICES COMPRISING FORCE MANAGEMENT FEATURES AND RELATED METHODS

TECHNICAL FIELD

Embodiments of the present disclosure relate generally to devices and methods for the closure of vascular openings. More specifically, embodiments of the present disclosure relate to vascular closure devices that include force management features, and methods of vascular closure.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture during certain points of the procedure or after the procedure has been completed. Bleeding from puncture sites, particularly in the case of femoral arterial punctures, is typically stopped by utilizing vascular closure devices.

One method of temporary vascular closure is to apply pressure to the interior wall of a lumen, such as a blood vessel, surrounding a puncture with a balloon attached to a catheter. The balloon is inserted through the puncture, after which the balloon is inflated within the lumen. A tensile force is then applied to the catheter by a surgeon to pull the inflated balloon against the interior of the lumen wall to temporarily close the puncture in the lumen wall. If a surgeon does not apply sufficient tensile force to the catheter, the balloon may not apply adequate pressure to the lumen wall to close the puncture. If a surgeon applies too much force to the catheter, however, the balloon may apply a pressure to the lumen wall that causes damage to the lumen wall and/or surrounding tissue. For example, if a surgeon applies too much force to the catheter it may cause separation of layers of the lumen wall, which may result in a hematoma or other complications.

SUMMARY

One aspect of the present disclosure relates to a vascular closure device comprising an elongate shaft, a vascular sealing structure, and a carriage. The vascular sealing structure may be located on the elongate shaft and configured to apply a pressure to an interior wall of a lumen. The carriage is slidably coupled to the elongate shaft. Additionally, at least one elastically deformable structure is configured to transfer at least a portion of a force applied to the carriage to the elongate shaft.

An additional aspect, which may be combined with other aspects herein, relates to the at least one elastically deformable structure comprising at least one spring coupled to the carriage and the elongate shaft. The at least one spring may include at least one extension spring. The at least one spring may include at least one compression spring. The at least one spring may include at least one torsion spring. The at least one elastically deformable structure may include at least one elastically deformable polymer structure coupled to the carriage and the elongate shaft. The vascular closure device may include a force indicator configured to indicate an amount of force applied to the elongate shaft via the carriage.

An additional aspect, which may be combined with other aspects herein, relates to the force indicator comprising a visual force indicator configured to provide a visual indication of an amount of force applied to the elongate shaft via the carriage. The visual force indicator may include at least one demarcation positioned to provide a visual indication of an amount of force applied to the elongate shaft via the carriage. The visual force indicator may include at least one light source configured to provide a visual indication of an amount of force applied to the elongate shaft via the carriage. The force indicator may include a tactile force indicator configured to provide a tactile indication of an amount of force applied to the elongate shaft via the carriage.

An additional aspect, which may be combined with other aspects herein, relates to the tactile force indicator comprising a vibration source configured to provide a tactile indication of an amount of force applied to the elongate shaft via the carriage. The force indicator may include an auditory force indicator configured to provide an auditory indication of an amount of force applied to the elongate shaft via the carriage. The vascular sealing structure may include a temporary vascular sealing structure. The temporary vascular sealing structure may include a balloon. The vascular sealing structure may include an implantable vascular sealing structure.

Another aspect of the present disclosure relates to a method of vascular closure. The method includes providing a vascular closure device that includes a vascular sealing structure positioned on an elongate shaft, a carriage slidably mounted to the elongate shaft, and at least one elastically deformable structure coupled between the carriage and the elongate shaft. The method also includes positioning a vascular sealing structure through a vessel puncture and into a vessel lumen, applying an axially directed force to the carriage, transferring at least a portion of the force applied to the carriage to the elongate shaft via the at least one elastically deformable structure, and applying a pressure to an interior wall of the vessel lumen with the vascular sealing structure to seal the vessel puncture.

An additional aspect, which may be combined with other aspects herein, relates to transferring at least a portion of the force applied to the carriage to the elongate shaft via at least one spring. The method may include determining an amount of force applied to the elongate shaft with a force indicator.

A further aspect of the present disclosure relates to a vascular closure device comprising an elongate shaft, a vascular sealing structure, a carriage, at least one elastically deformable structure, and a force indicator. The vascular sealing structure is positioned on the elongate shaft and configured to apply pressure to an interior wall of a vessel lumen. The carriage is slidably mounted to the elongate shaft. The at least one elastically deformable structure is coupled between the carriage and the elongate shaft and is configured to transfer at least a portion of a force applied to the carriage to the elongate shaft. The force indicator is configured to indicate an amount of pressure applied to the elongate shaft.

BRIEF DESCRIPTION OF THE DRAWINGS

The accompanying drawings illustrate various embodiments of the present methods and systems and are a part of the specification. The illustrated embodiments are merely examples of the present systems and methods and do not limit the scope thereof.

FIG. 9 is a side view of a vascular closure device showing a cutaway of a carriage slidably coupled to an elongate shaft of the vascular closure device via extension springs, and an audible force indicator including an electronic buzzer.

FIG. 10 is a side view of the vascular closure device of FIG. 9, wherein the carriage has been moved relative to the elongate shaft and the extension springs are extended.

DETAILED DESCRIPTION

The devices and systems disclosed herein may be used to close or seal percutaneous punctures made through the body tissue of a patient to gain access to a body cavity of a patient. Access through these percutaneous punctures allows a surgeon to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other surgery techniques using a relatively small incision.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "tube" is an elongated device with a passageway. The passageway may be enclosed or open (e.g., a trough). A "lumen", when referring to a bodily organ, refers to any open space or cavity in the bodily organ, especially in a blood vessel. The words "including" and "having," as well as their derivatives, as used in the specification, including the claims, have the same meaning as the word "comprising."

Figure 1:
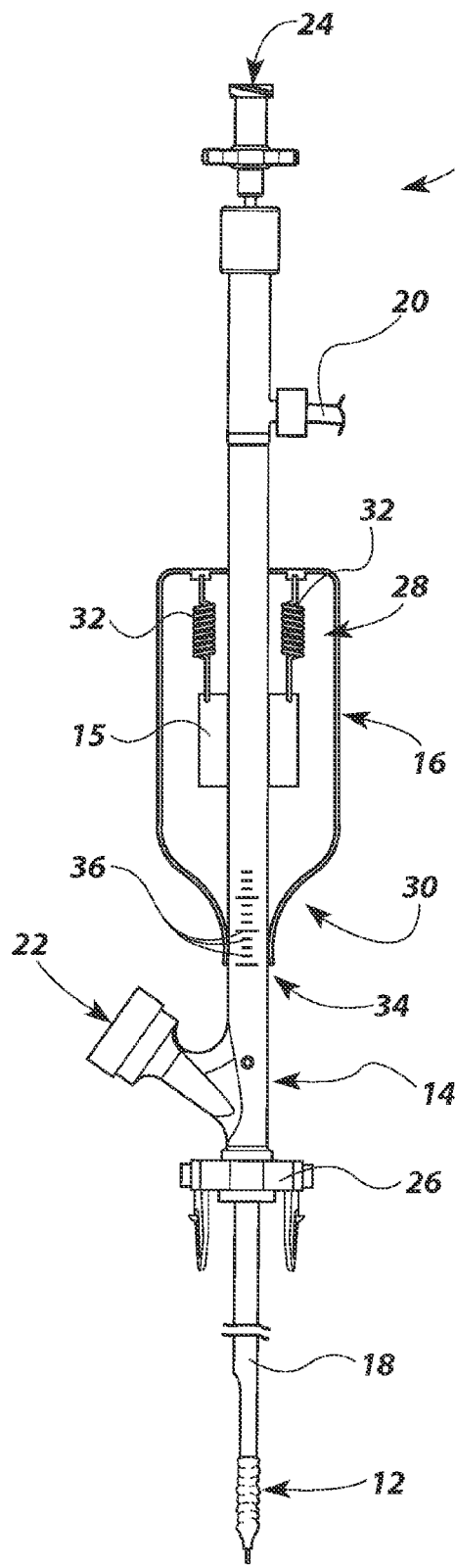
FIG. 1 is a side view of a vascular closure device showing a cutaway of a carriage slidably coupled to an elongate shaft of the vascular closure device via extension springs, and a visual force indicator including a plurality of lines.
Figure 2:
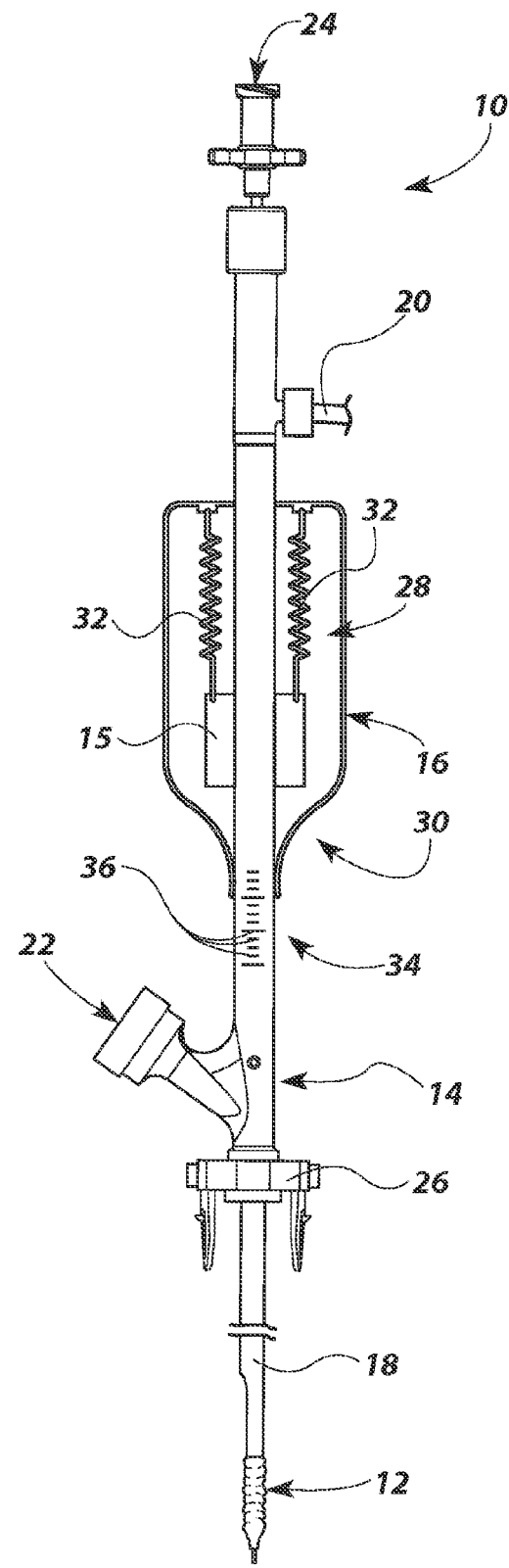
FIG. 2 is a side view of the vascular closure device of FIG. 1, wherein the carriage has been moved relative to the elongate shaft and the extension springs are extended.

In one embodiment, as shown in FIGS. 1 and 2, a vascular closure device 10 may comprise a vascular sealing structure (i.e., a balloon 12) located at a distal region of an elongate shaft 14. The vascular closure device 10 may additionally include a carriage 16 slidably coupled to a proximal region of the elongate shaft 14. While in some embodiments the carriage 16 may be slidably coupled directly to the elongate shaft 14, in further embodiments the carriage 16 may be slidably coupled to an intermediate structure that is fixed relative to the elongate shaft 14.

A vascular sealing structure may be configured to provide a selective and temporary seal of a vascular puncture. For example, the vascular sealing structure may comprise a balloon 12, as shown in FIGS. 1 and 2, which may be selectively inflated and deflated. In further embodiments, a vascular sealing structure may be an implantable vascular sealing structure, such as an implantable anchor device (not shown).

Figure 11:
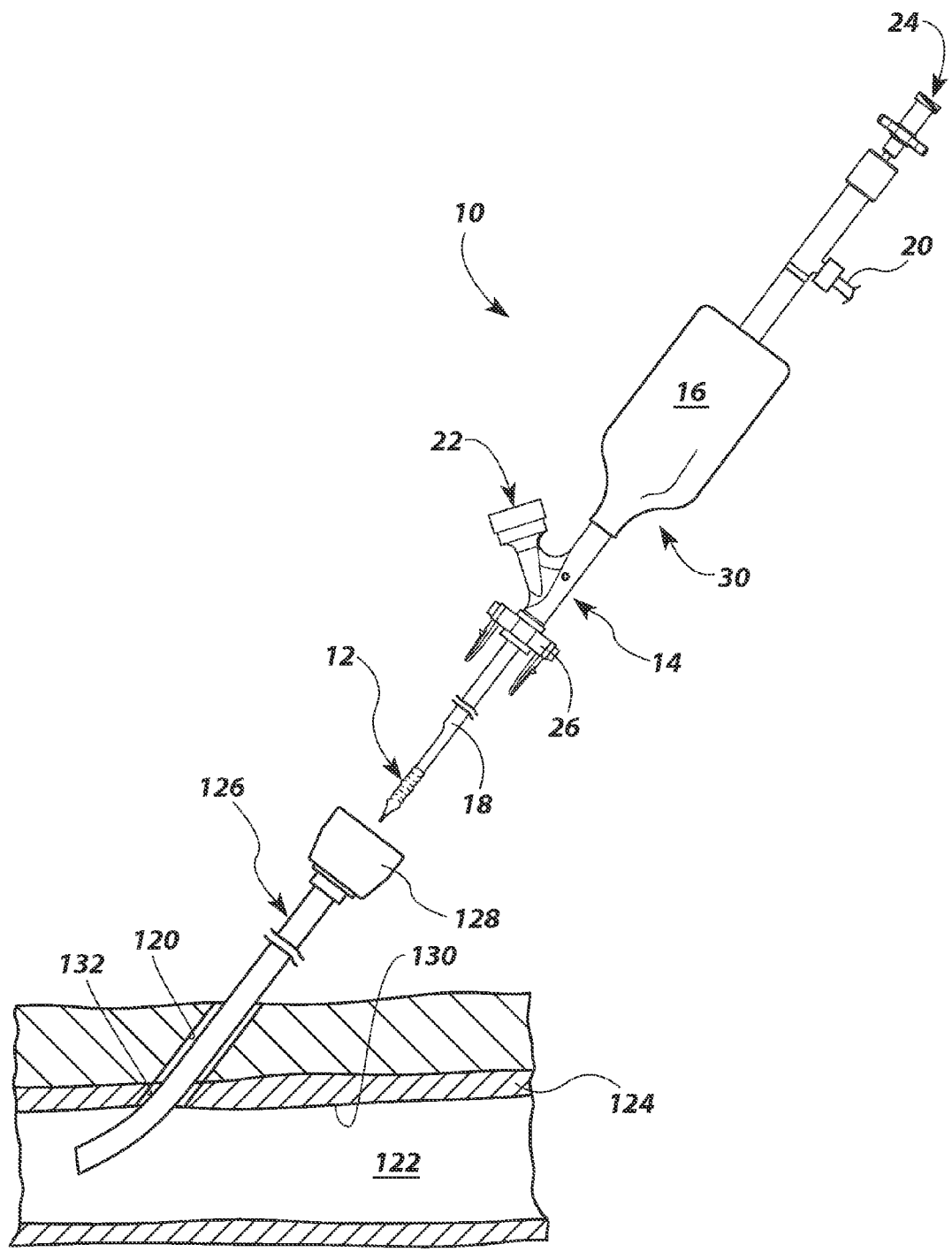
FIG. 11 is a side view of the vascular closure device of FIG. 1 being inserted into a vascular opening.
Figure 12:
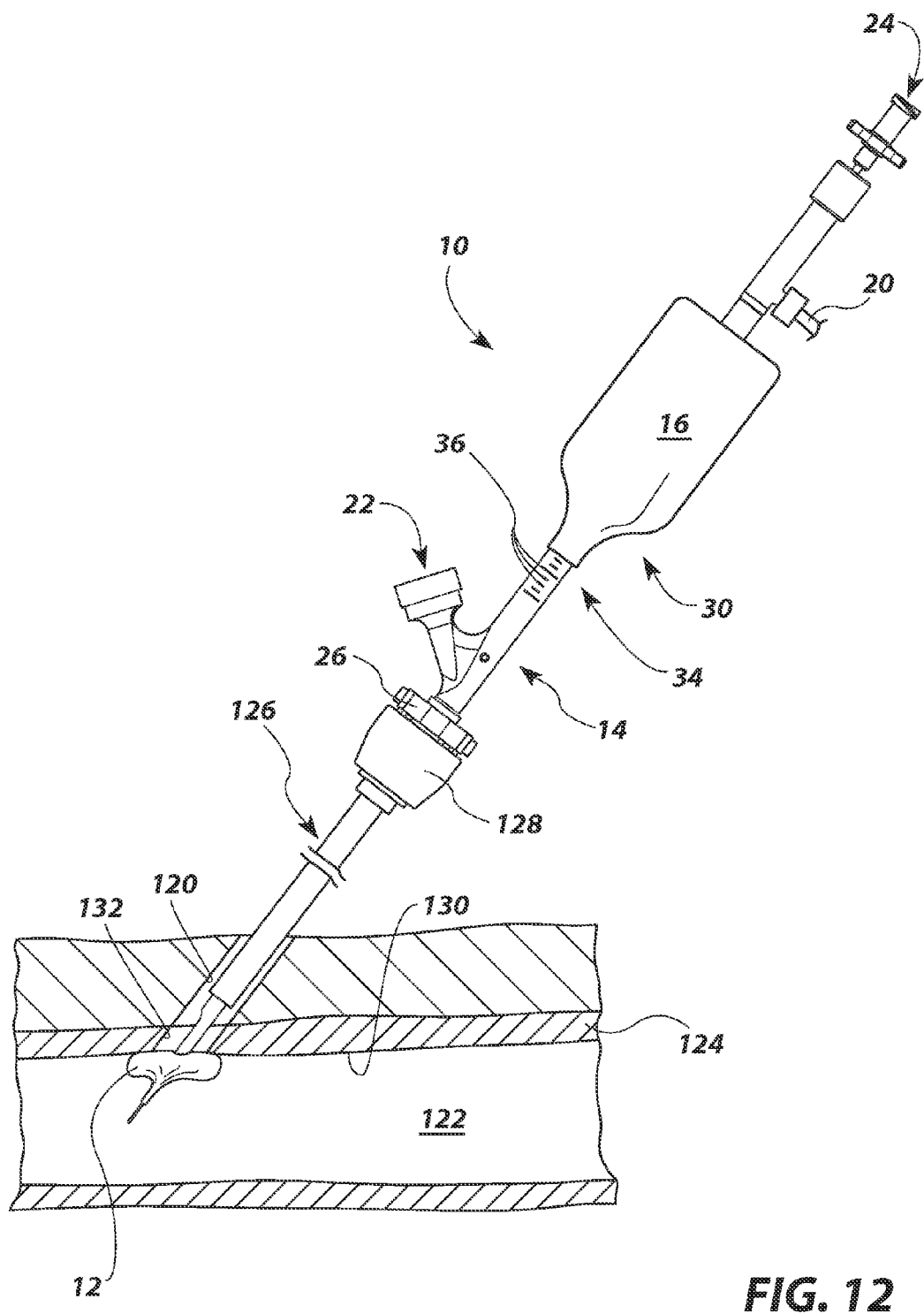
FIG. 12 is a side view of the vascular closure device of FIG. 1 wherein a balloon at a distal end has been pulled against a vascular wall via the carriage to seal the vascular opening.

The elongate shaft 14 may be configured to extend through a tissue tract 120 and vascular opening 132 into a lumen 122 of a patient (see FIGS. 11 and 12). The distal portion of the elongate shaft 14 may be configured to extend into the patient's body, while the proximal end of the elongate shaft 14 extends out of the patients body and is accessible for manipulation by a surgeon.

The elongate shaft 14 may comprise a catheter 18 having one or more tubes extending therethrough. A tube in the catheter 18 may facilitate the transfer of fluid between the balloon 12 and a fluid source 20 for the selective inflation and deflation of the balloon 12. Additional tubes, which may be accessible through openings 22 and 24 in the catheter 18, may facilitate the delivery of fluids, such as medications, saline solution, bioadhesives, and the like, at the distal end of the catheter 18 and into a patient's body.

The elongate shaft 14 may also include a guide wire (not shown), which may facilitate the positioning of the distal end of the elongate shaft 14 within a patient's body, such as within a lumen 122 of a blood vessel 124 (see FIGS. 11 and 12). Additionally, the distal end of the elongate shaft 14 may be sized and configured to fit through a sheath 126 (see FIGS. 11 and 12) and a coupler 26 fixed to the elongate shaft 14 may be configured to be selectively coupled to the sheath 126.

The carriage 16 may surround a portion of the elongate shaft 14. At least one elastically deformable member 28 may extend between the carriage 16 and the elongate shaft 14. One end of the elastically deformable member 28 may be connected to an end of the carriage 16 and an opposite end of the elastically deformable member 28 may be connected to the elongate shaft 14. The elastically deformable member 28 may be coupled to the elongate shaft 14 with a connector member 15 (see FIGS. 1-8), which is fixed to the elongate shaft 14.

Figure 6:
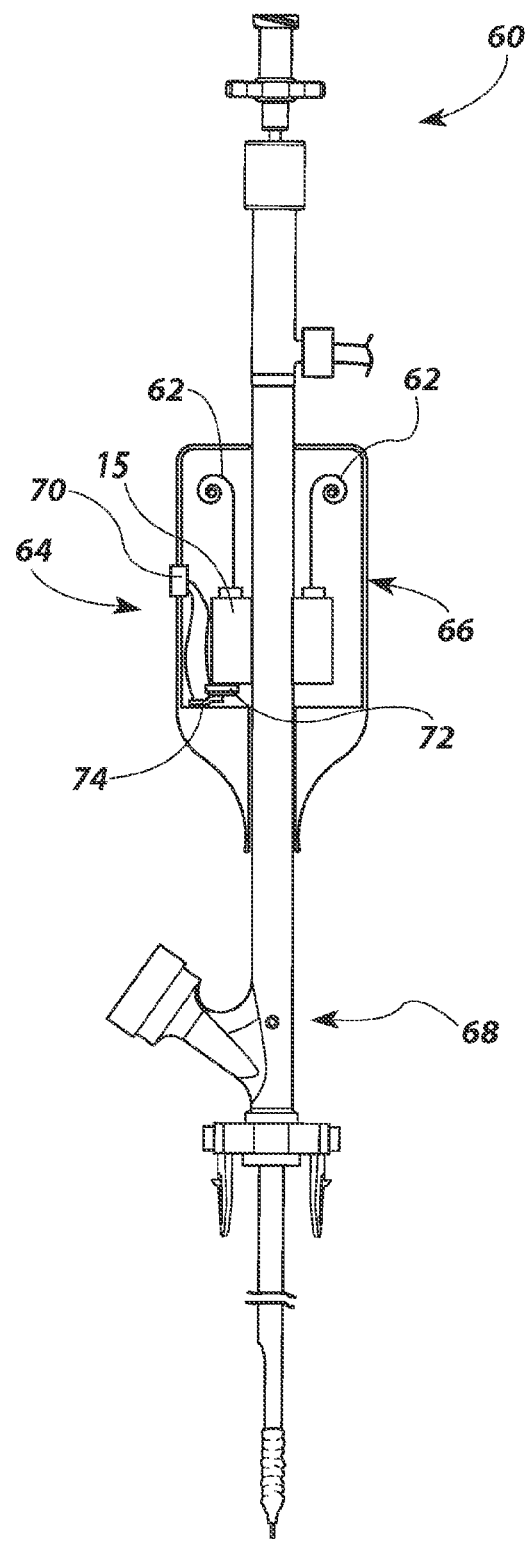
FIG. 6 is a side view of the vascular closure device of FIG. 5, wherein the carriage has been moved relative to the elongate shaft and the torsion springs are extended.
Figure 7:
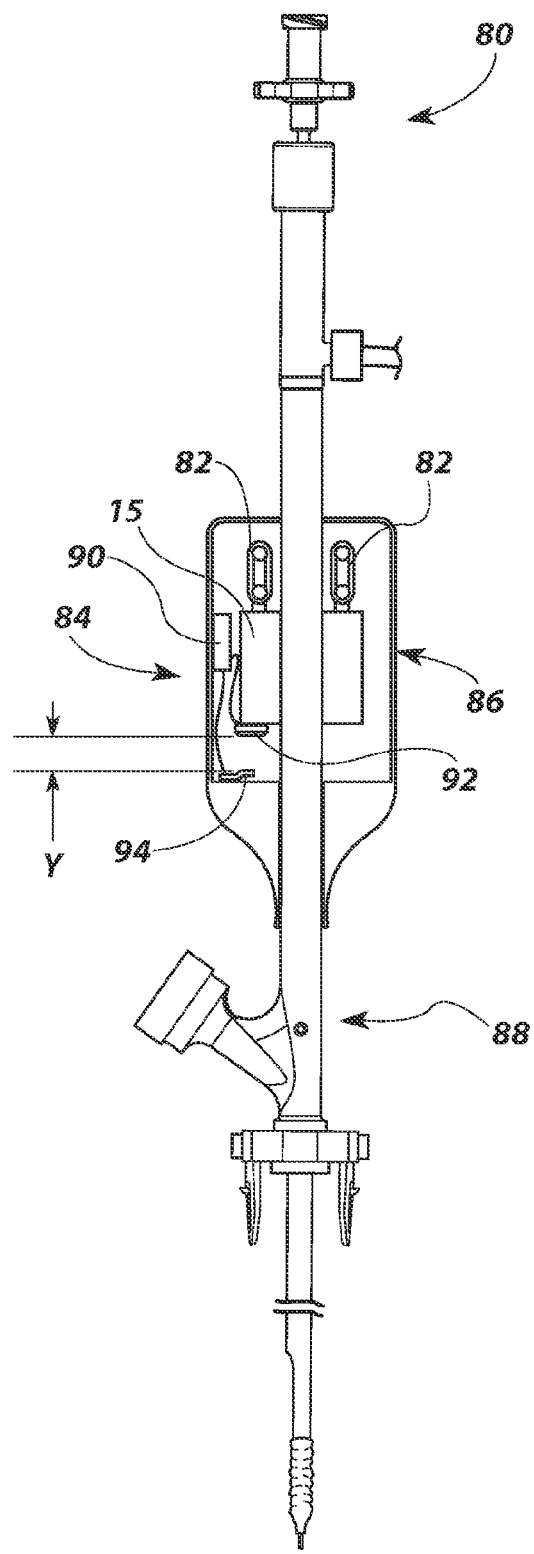
FIG. 7 is a side view of a vascular closure device showing a cutaway of a carriage slidably coupled to an elongate shaft of the vascular closure device via rubber bands, and a tactile force indicator including a vibration source.
Figure 8:
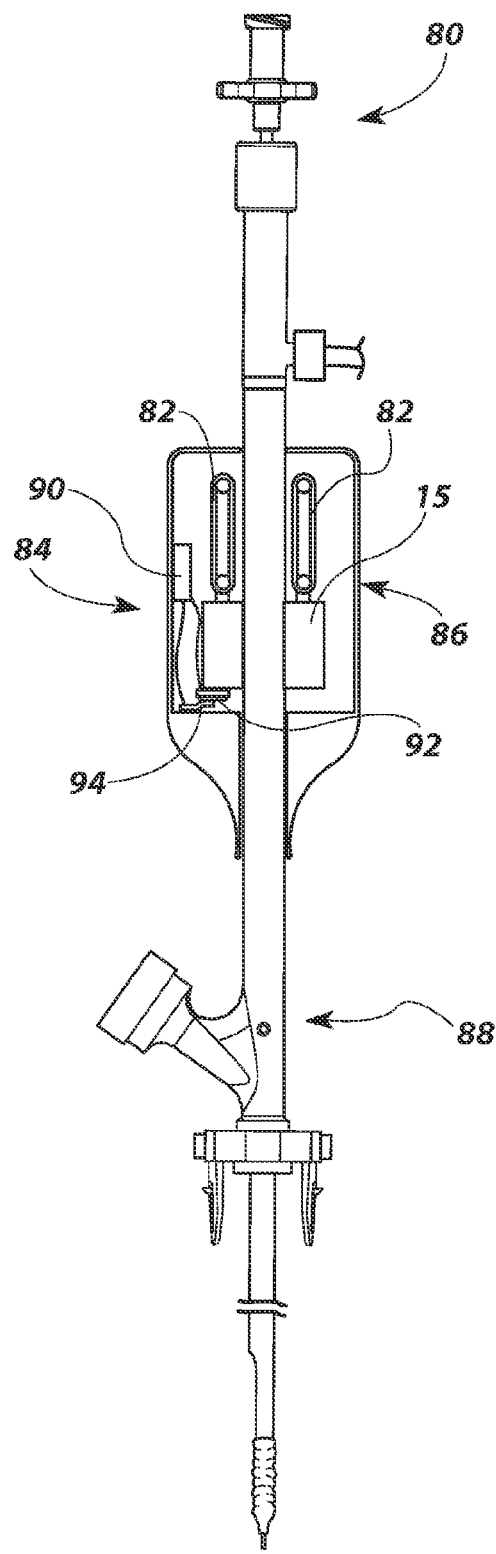
FIG. 8 is a side view of the vascular closure device of FIG. 7, wherein the carriage has been moved relative to the elongate shaft and the rubber bands are extended.

Provided as examples, and not as limitations, an elastically deformable member 28 may comprise one or more of an extension spring 32 (see FIGS. 1, 2, 9 and 10), a compression spring 42 (see FIGS. 3 and 4), a torsion spring 62 (see FIGS. 5 and 6), and an elastically deformable polymer structure (e.g., a rubber band 82) (see FIGS. 7 and 8). The carriage 16 may include a finger grip portion 30 configured to facilitate grasping and pulling of the carriage 16 by a surgeon. As clearly shown in FIGS. 7 and 8, each elastically deformable member 28 is laterally offset from the longitudinal axes of the elongate shaft 14 and the carriage 16.

As shown in FIGS. 1 and 2, the at least one elastically deformable member 28 may comprise at least one extension spring 32 configured to elastically elongate under a tensile force. A certain amount of deformation of the elastically deformable member 28 (e.g., a percentage of elongation of each extension spring 32) may correspond to a specific tensile force applied to the elastically deformable member 28. Accordingly, for a specific force applied to the elongate shaft 14 via the carriage 16, the carriage 16 will move a corresponding distance relative to the elongate shaft 14.

To facilitate an appropriate application of force for vascular closure, the vascular closure device 10 may include a force indicator 34 configured to indicate an amount of force applied to the elongate shaft 14, and thus the vascular sealing structure (e.g., the balloon 12), via the carriage 16. The force indicator 34 may be a visual force indicator that comprises visual demarcations.

A region of the vascular closure device 10 that is fixed relative to the elongate shaft 14 may include visual demarcations that correspond to displacement distances of the carriage 16 relative to the elongate shaft 14 when various forces are applied to the carriage 16. For example, a plurality of lines 36 may be marked on the elongate shaft 14, or on a region of the vascular closure device 10 that is fixed relative to the elongate shaft 14. Optionally, one or more lines may be marked on the carriage 16.

When a force is applied to the carriage 16, a force may be transferred to the elongate shaft 14 via each elastically deformable member 28. Each extension spring 32 may deform under the applied force, and the carriage 16 may slide relative to the elongate shaft 14. The magnitude of the applied force may then be determined by examining the movement of the carriage 16 relative to the elongate shaft 14 by observing the location of a line of the plurality of lines 36 relative to the carriage 16.

Figure 3:
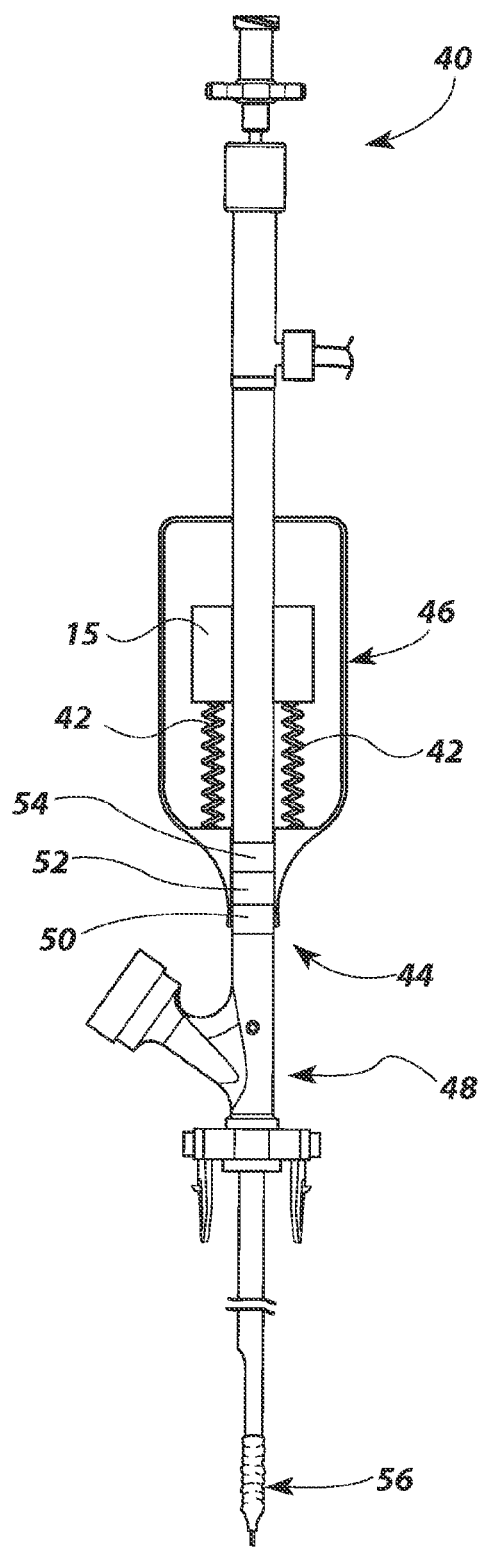
FIG. 3 is a side view of a vascular closure device showing a cutaway of a carriage slidably coupled to an elongate shaft of the vascular closure device via compression springs, and a visual force indicator including marked regions.
Figure 4:
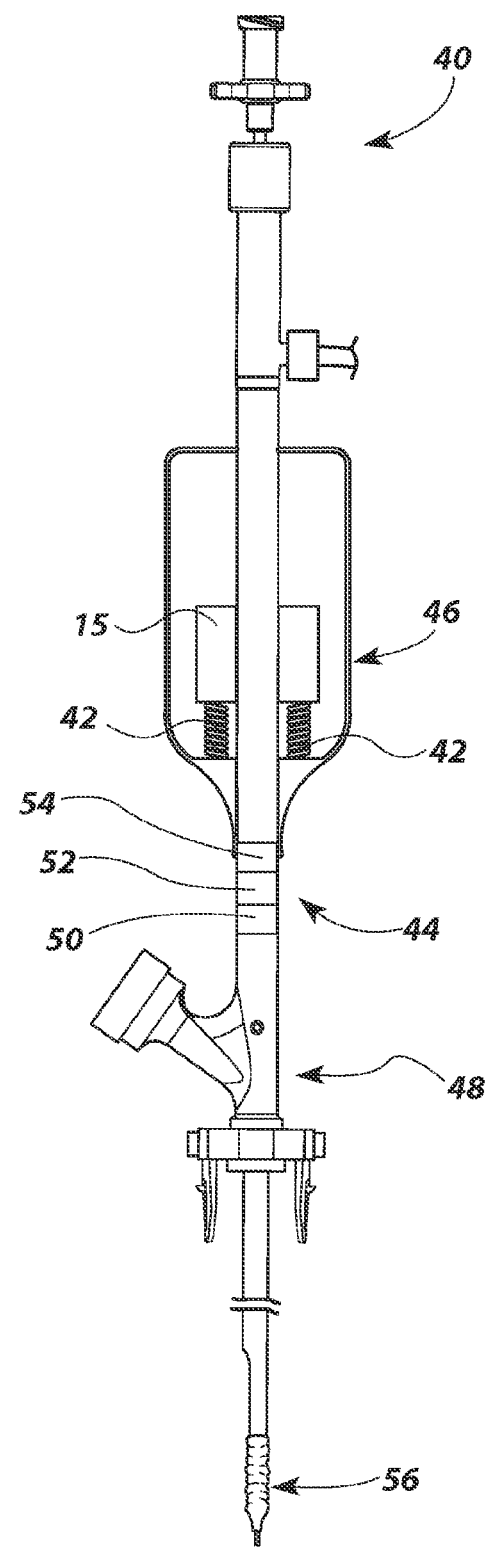
FIG. 4 is a side view of the vascular closure device of FIG. 3, wherein the carriage has been moved relative to the elongate shaft and the compression springs are compressed.

In further embodiments, a visual force indicator 44 may be configured to indicate ranges of forces applied to a vascular closure device 40, as shown in FIGS. 3 and 4. For example, visual demarcations may comprise marked regions 50, 52 and 54 over specific areas that correspond to a range of movement of a carriage 46 relative to an elongate shaft 48.

A first marked region 50 may indicate a range of relative movement of the carriage 46 relative to the elongate shaft 48 that results when an applied force is relatively small and may be insufficient to facilitate complete closure of a vascular puncture with a balloon 56 at the distal end of the elongate shaft 48.

A second marked region 52 may indicate a range of relative movement of the carriage 46 relative to the elongate shaft 48 that results when an applied force is in a desirable range, wherein the force may be sufficient to facilitate complete closure of a vascular puncture with the balloon 56 at the distal end of the elongate shaft 48 without causing injury to the patient.

A third marked region 54 may indicate a range of relative movement of the carriage 46 relative to the elongate shaft 48 that results when an applied force is beyond the desirable range, wherein the force may cause the balloon 56 at the distal end of the elongate shaft 48 to cause injury to the patient.

The first, second, and third marked regions 50, 52 and 54 may each be distinctly colored to visually differentiate each marked region. In one embodiment, the third marked region 54 may be colored red, which may indicate to a surgeon that the currently applied force is too high and to reduce the amount of force being applied to the carriage 46. The second marked region 52 may be marked the color green, which may indicate to a surgeon that the currently applied force is sufficient and to maintain the amount of force being applied to the carriage 46. The first marked region 50 may be marked a color other than red or green, such as blue or yellow, which may indicate to the surgeon that the currently applied force may be too low to achieve hemostasis and to increase the force being applied to the carriage 46.

It will be understood by persons of ordinary skill in the art that colors different than those described with reference to this embodiment may be effectively utilized in additional embodiments. In yet further embodiments, instead of colors, or in addition to colors, other visual demarcations may be utilized to distinguish each of the first, second, and third marked regions 50, 52 and 54, such as one or more of symbols, textures and patterns.

Figure 5:
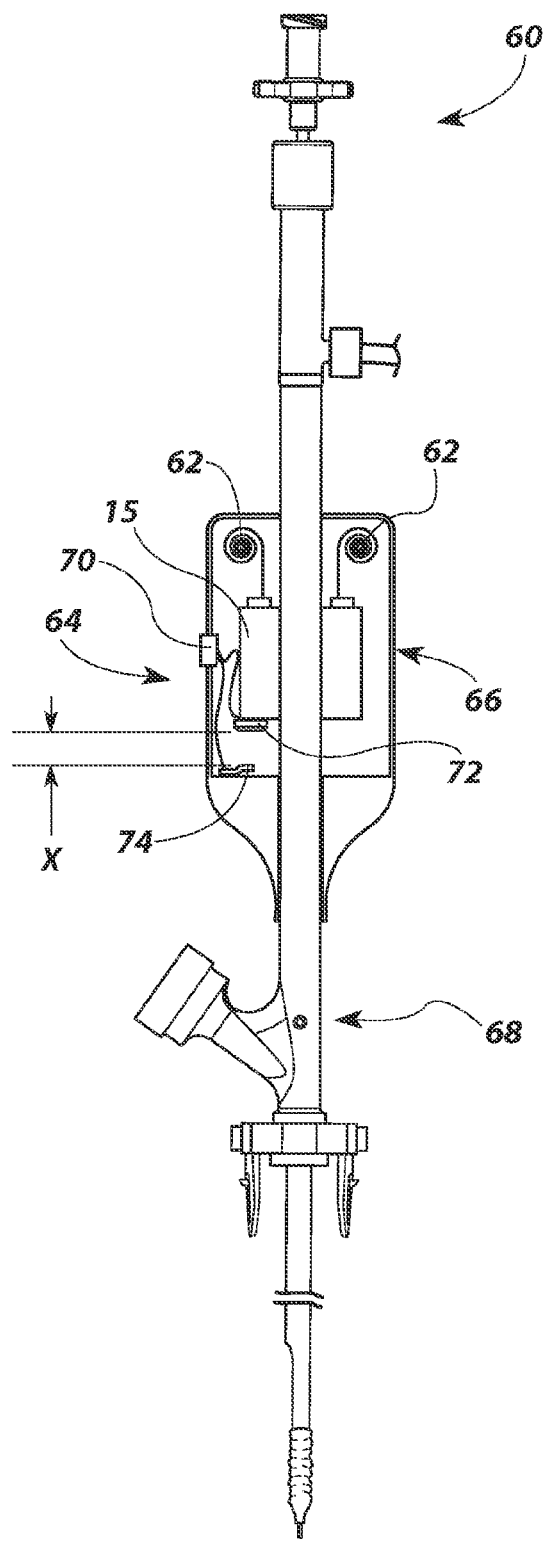
FIG. 5 is a side view of a vascular closure device showing a cutaway of a carriage slidably coupled to an elongate shaft of the vascular closure device via torsion springs, and a visual force indicator including a light source.

In some embodiments, as shown in FIGS. 5 and 6, a visual force indicator 64 may comprise at least one light source configured to provide a visual indication of an amount of force applied to an elongate shaft 68 via a carriage 66. For example, a vascular closure device 60 may include a light source, a power source, and a switch. The light source may be a light emitting diode (LED) 70 positioned to be visible to a surgeon when operating the vascular closure device 60. The power source may be a battery 72. The switch may be an electrical contact 74 positioned to come into contact with the battery 72 and complete a circuit between the LED 70 and the battery 72 when the carriage 66 has moved a distance X relative to the elongate shaft 68.

The distance X may correspond to a distance at which elastic members (e.g., torsion springs 62) are deformed when a specific force has been applied. For example, the distance X may correspond to a distance that the carriage 66 travels relative to the elongate shaft 68 when a threshold force corresponding to risk of injury to a patient has been applied to the vascular closure device 60. Accordingly, if a surgeon applies a force to the carriage 66 that is sufficient to cause the carriage 66 to move the distance X, relative to the elongate shaft 68, the electrical contact 74 may close a circuit between the LED 70 and the battery 72 and the LED 70 may illuminate. The illumination of the LED 70 may provide a visual alert to the surgeon that a threshold force has been reached, and that an increased or sustained application of force to the vascular closure device 60 may be harmful to the patient.

In some embodiments, as shown in FIGS. 7 and 8, a tactile force indicator 84 may comprise at least one tactile feedback source, such as a vibrating device 90, configured to provide a tactile sensation (e.g., vibrations) to indicate an amount of force applied to an elongate shaft 88 via a carriage 86.

For example, a vascular closure device 80 may include a tactile source, a power source, and a switch. The tactile source may be the vibrating device 90 (e.g., a piezoelectric device) positioned to deliver a vibration that may be felt by a surgeon when operating the vascular closure device 80. The power source may be a battery 92. The switch may be an electrical contact 94 positioned to come into contact with the battery 92 and complete a circuit between the vibrating device 90 and the battery 92 when the carriage 86 has moved a distance Y relative to the elongate shaft 88.

The distance Y may correspond to a distance at which elastic members (e.g., the rubber bands 82) are deformed when a threshold force has been applied. For example, the distance Y may correspond to a distance that the carriage 86 travels relative to the elongate shaft 88 when a threshold force corresponding to risk of injury to a patient has been applied to the vascular closure device 80. Accordingly, if a surgeon applies a force to the carriage 86 that is sufficient to cause the carriage 86 to move the distance Y relative to the elongate shaft 88, the electrical contact 94 may close a circuit between the vibrating device 90 and the battery 92 and the vibrating device 90 may produce vibrations. The vibrations may provide a tactile alert to the surgeon that a threshold force has been reached, and that an increased or sustained application of force to vascular closure device 80 may be harmful to the patient.

In some embodiments, as shown in FIGS. 9 and 10, a vascular closure device 100 may comprise an auditory force indicator 102. The auditory force indicator 102 may comprise at least one auditory source configured to provide an auditory indication of an amount of force applied to an elongate shaft 104 via a carriage 106. For example, the auditory force indicator 102 may include an auditory source, a power source, and a switch. The auditory source may be an electronic buzzer 108 positioned to deliver an audible buzz that may be heard by a surgeon when operating the vascular closure device 10. The power source may be a battery 110. The switch may be an electrical contact 112 positioned to come into contact with the battery 110 and complete a circuit between the electronic buzzer 108 and the battery 110 when the carriage 106 has moved a distance Z relative to the elongate shaft 104.

The distance Z may correspond to a distance at which elastic members (e.g., the extension springs 114) are deformed when a threshold force has been applied. For example, the distance Z may correspond to a distance that the carriage 106 travels relative to the elongate shaft 104 when a threshold force corresponding to risk of injury to a patient has been applied to the vascular closure device 100. Accordingly, if a surgeon applies a force to the carriage 106 that is sufficient to cause the carriage 106 to move the distance Z, the electrical contact 112 may close a circuit between the electronic buzzer 108 and the battery 110 and the electronic buzzer 108 may produce an audible sound. The audible sound may alert the surgeon that a threshold force has been reached, and that an increased or sustained application of force to vascular closure device 100 may be harmful to the patient.

Referring to FIG. 11, a method of vascular closure may comprise positioning a vascular sealing structure, such as the balloon 12, located on the elongate shaft 14 of the vascular closure device 10 through a tissue tract 120, through a vascular opening 132, and within a lumen 122 of a blood vessel 124. The distal end of the elongate shaft 14 may be positioned within a sheath 126 and the coupler 26 of the vascular closure device 10 may be aligned with a receiving collar 128 on the sheath 126 to couple the elongate shaft 14 to the sheath 126.

As shown in FIG. 12, after the coupler 26 of the vascular closure device 10 and the receiving collar 128 of the sheath 126 have been coupled together, and the distal end of the elongate shaft 14 has been inserted into the lumen 122, the balloon 12 may be inflated. A retraction force (e.g., a proximally directed force) may then be applied to the carriage 16 by a surgeon. At least a portion of the retraction force may be transferred to the elongate shaft 14 via the at least one elastically deformable structure (e.g., the extension springs 32). The balloon 12 may then abut against and apply a pressure to an interior wall 130 of the blood vessel 124. The balloon 12 may at least partially close the vascular opening 132. Finally, an amount of force that is applied to the elongate shaft 14 via the carriage 16, and thus to the interior wall 130 of the blood vessel 124 via the balloon 12, may then be determined by utilizing the force indicator 34.

If the force indicator 34 indicates that the force applied to the vascular closure device 10 may be insufficient to fully seal the vascular opening 132, additional force may be applied to the carriage 106 by the surgeon. If the force indicator 34 indicates that excessive force is being applied to the vascular closure device 10, which may potentially harm the patient, the surgeon may reduce the amount of force that is being applied to the carriage 16. If the force indicator 34 indicates that the force being applied is appropriate to provide hemostasis without significant risk of harm to the patient, the surgeon may maintain the force being applied to the carriage 16 for the remaining portion of the procedure that requires the hemostasis. Additionally, the force applied to the vascular closure device 10 via the carriage 16 may be regularly monitored throughout the procedure via the force indicator 34. Accordingly, an effective closure of the vascular opening 132 may be achieved without the application of an amount of force that may be harmful to the patient.

The preceding description has been presented only to illustrate and describe example embodiments of the invention. It is not intended to be exhaustive or to limit the invention to any precise form disclosed. Many modifications and variations are possible in light of the above teachings. It is intended that the scope of the invention be defined by the following claims.

What is claimed is:

1. A vascular closure device, comprising:
    an elongate shaft configured to extend through a vascular puncture in a vessel, the elongate shaft having a longitudinal axis;
    a vascular sealing structure positioned on the elongate shaft and configured to provide temporary hemostasis of the vascular puncture by sealing against an interior wall of the vessel;
    a carriage mounted to, slidably coupled to, and in direct contact with the elongate shaft;
    at least one elastically deformable structure coupled between the elongate shaft and the carriage and configured to transfer forces applied to the carriage to the elongate shaft, the at least one elastically deformable structure being laterally offset from the longitudinal axis;
    wherein the carriage is slidable relative to the elongate shaft to close an electrical circuit and measure a force applied to the vascular closure device.

2. The vascular closure device of claim 1, wherein the at least one elastically deformable structure comprises at least one spring coupled to the carriage and to the elongate shaft.

3. The vascular closure device of claim 2, wherein the at least one spring comprises at least one extension spring.

4. The vascular closure device of claim 2, wherein the at least one spring comprises at least one compression spring.

5. The vascular closure device of claim 2, wherein the at least one spring comprises at least one torsion spring.

6. The vascular closure device of claim 1, wherein the at least one elastically deformable structure comprises at least one elastically deformable polymer structure coupled to the carriage and the elongate shaft.

7. The vascular closure device of claim 1, further comprising a force indicator configured to indicate an amount of force applied to the elongate shaft via the carriage.

8. The vascular closure device of claim 7, wherein the force indicator comprises a visual force indicator configured to provide a visual indication of an amount of force applied to the elongate shaft via the carriage.

9. The vascular closure device of claim 8, wherein the visual force indicator comprises at least one demarcation positioned to provide a visual indication of an amount of force applied to the elongate shaft via the carriage.

10. The vascular closure device of claim 8, wherein the visual force indicator comprises at least one light source configured to provide a visual indication of an amount of force applied to the elongate shaft via the carriage.

11. The vascular closure device of claim 7, wherein the force indicator comprises a tactile force indicator configured to provide a tactile indication of an amount of force applied to the elongate shaft via the carriage.

12. The vascular closure device of claim 11, wherein the tactile force indicator comprises a vibration source configured to provide a tactile indication of an amount of force applied to the elongate shaft via the carriage.

13. The vascular closure device of claim 7, wherein the force indicator comprises an auditory force indicator configured to provide an auditory indication of an amount of force applied to the elongate shaft via the carriage.

14. The vascular closure device of claim 1, wherein the vascular sealing structure comprises a temporary vascular sealing structure.

15. The vascular closure device of claim 14, wherein the temporary vascular sealing structure comprises a balloon.

16. The vascular closure device of claim 1, wherein the vascular sealing structure comprises an implantable vascular sealing structure.

17. A vascular closure device, comprising:
an elongate shaft having a longitudinal axis;
a vascular sealing structure positioned on the elongate shaft and configured to apply pressure to an interior wall of a vessel lumen;
a carriage mounted to, slidably coupled to, and in direct contact with the elongate shaft;
a switch, the switch being configured to close an electrical circuit in response to movement of the carriage relative to the elongate shaft;
at least one elastically deformable structure coupled between the carriage and the elongate shaft, the at least one elastically deformable structure configured to transfer at least a portion of a force applied to the carriage to the elongate shaft, the at least one elastically deformable structure being laterally offset from the longitudinal axis;
a force indicator configured to indicate an amount of pressure applied to the elongate shaft in response to closure of the electrical circuit.

* * * * *